(12) United States Patent
Wang et al.

(10) Patent No.: US 6,214,854 B1
(45) Date of Patent: Apr. 10, 2001

(54) METHOD FOR INHIBITING STRESS-ACTIVATED PROTEIN KINASES

(75) Inventors: Xinkang Wang, Berwyn; Tian-Li Yue, Havertown, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/456,866

(22) Filed: Dec. 8, 1999

Related U.S. Application Data

(63) Continuation of application No. 09/284,223, filed as application No. PCT/US97/18272 on Oct. 9, 1997.
(60) Provisional application No. 60/028,459, filed on Oct. 9, 1996.

(51) Int. Cl.[7] .................................................. A61K 31/40
(52) U.S. Cl. .............................................................. 514/411
(58) Field of Search ............................................... 514/411

(56) References Cited

U.S. PATENT DOCUMENTS

| | | |
|---|---|---|
| 4,503,067 | 3/1985 | Wiedemann et al. . |
| 5,308,862 | 5/1994 | Ohlstein . |
| 5,393,772 | 2/1995 | Yue et al. . |
| 5,405,863 | 4/1995 | Barone et al. . |
| 5,453,436 | 9/1995 | Ohlstein . |
| 5,643,915 | 7/1997 | Andrulis, Jr. et al. . |
| 5,643,939 | 7/1997 | Ohlstein . |

OTHER PUBLICATIONS

Yue, et al., Chen. Abstracts, 1994, vol. 120, No. 19, Abstract No. 235718a.
Feuerstein, et al., Chem. Abstracts, 1994, vol. 121, No. 3, Abstract No. 26572e.
Yue, et al., Chem. Abstracts, 1994, vol. 121, No. 9, Abstract No. 99392f.
Ohta, et al., Chem. Abstracts, 1995, vol. 122, No. 3, Abstract No. 29762y.
Brunvand, et al., Chem. Abstracts, 1996, vol. 125, No. 19, Abstract No. 238026n.
Morooka et al. Ischemia and reperfusion . . . , J. Biol. Chem. vol. 270/50, pp. 30084–30092, 1995.*
Kyriakis et al., P54 stress–activated protein kinases and . . . , Can. Patent abstract (CA 2148898)–1995.*

\* cited by examiner

*Primary Examiner*—William R. A. Jarvis
*Assistant Examiner*—Vickie Kim
(74) *Attorney, Agent, or Firm*—Mary E. McCarthy; Stephen Venetianer; Charles M. Kinzig

(57) ABSTRACT

This invention relates to a method for inhibiting stress-activated protein kinases (SAPKs) which comprises administering to a mammal in need thereof an effective amount of a compound which is a dual non-selective $\beta$-adrenoceptor and $\alpha_1$-adrenoceptor antagonist.

4 Claims, 1 Drawing Sheet

METHOD FOR INHIBITING STRESS-ACTIVATED PROTEIN KINASES

Figure 1:
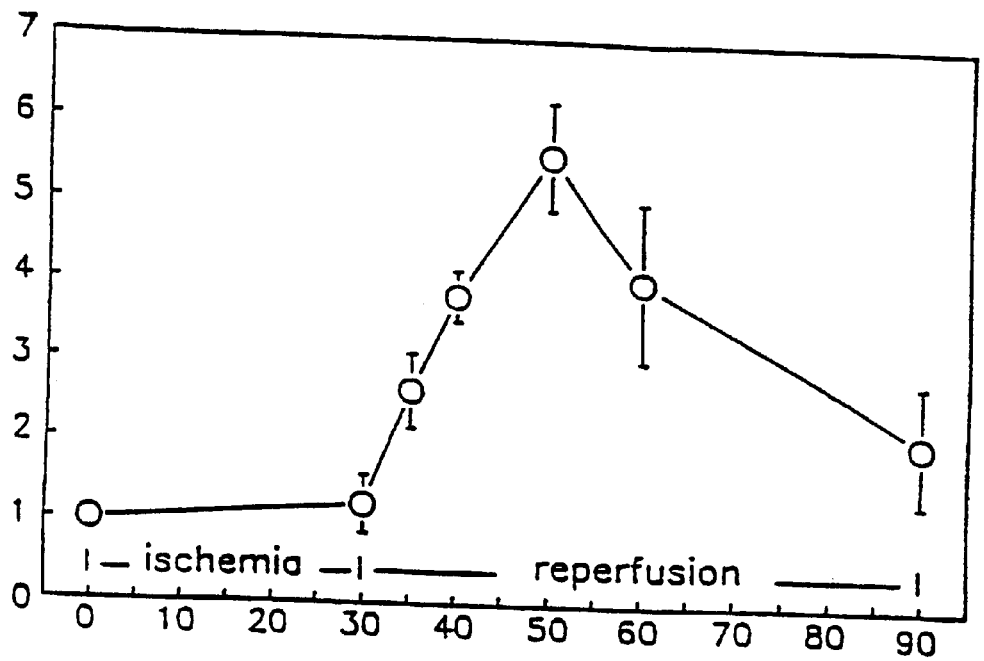

This is a continuation of application Ser. No.: 09/284,223, filed Apr. 9, 1999, which is a 371 of PCT/US97/18272, filed Oct. 9, 1997; which claims the benefit of Provisional application No. 60/028,459, filed Oct. 9, 1996.

FIELD OF THE INVENTION

The present invention relates to a new method of treatment using compounds which are dual non-selective β-adrenoceptor and α$_1$-adrenoceptor antagonists, in particular the carbazolyl-(4)-oxypropanolamine compounds of Formula I, preferably carvedilol, for inhibiting stress-activated protein kinases (SAPKs). This invention also relates to a method of treatment using compounds which are dual non-selective β-adrenoceptor and α$_1$-adrenoceptor antagonists, in particular the carbazolyl-(4)-oxypropanolamine compounds of Formula I, preferably carvedilol, for treating diseases mediated by stress-activated protein kinases.

BACKGROUND OF THE INVENTION

Cells respond to extracellular stimuli by activating signal transduction pathways, which culminate in gene expression. A critical component of eukaryotic signal transduction is the activation of protein kinases, which phosphorylate a host of cellular substrates. Certain protein serine/threonine kinases transduce signals to the nucleus of cells in response to cellular stresses. These kinases are known as stress-activated protein kinases (SAPKs), or, alternately, c-Jun N-terminal (amino-terminal kinases (JNKs), and likely play a role in the genetic response of many components of the cardiovascular system to disease processes [Force, et al., Circulation Research, 78(6): 947–953 (1996)]. Stress-activated protein kinases activate genes responsible for apoptosis (cell death); SAPK activation precedes the onset of apoptosis.

Surprisingly, it has been found that carvedilol, a dual non-selective β-adrenoceptor and α$_1$-adrenoceptor antagonist, inhibits stress-activated protein kinases. This inhibition means that carvedilol and related Formula I compounds are useful in treating diseases mediated by stress-activated protein kinases. Importantly, this inhibition means that carvedilol and related Formula I compounds are useful for treating SAPK-initiated apoptosis. This inhibition also means that carvedilol and related Formula I compounds are useful for treating cardiovascular diseases, such as ischemia, atherosclerosis, heart failure, and restenosis.

SUMMARY OF THE INVENTION

The present invention provides a new method of treatment using compounds which are dual non-selective β-adrenoceptor and a α$_1$-adrenoceptor antagonists, in particular the carbazolyl-(4)-oxypropanolamine compounds of Formula I, preferably carvedilol, for inhibiting stress-activated protein kinases, in mammals, particularly humans. The present invention also provides a method of treatment using said compounds for treating diseases mediated by stress-activated protein kinases. Additionally, this invention provides a method for treating SAPK-initiated apoptosis using the compounds of Formula I. This invention further provides a method of treatment using dual non-selective β-adrenoceptor and α$_1$-adrenoceptor antagonists, in particular carvedilol, in the treatment of cardiovascular disorders, such as ischemia, atherosclerosis, heart failure, and restenosis following angioplasty.

DETAILED DESCRIPTION OF THE INVENTION

The present invention provides a new method for inhibiting stress-activated protein kinases using compounds which are dual non-selective β-adrenoceptor and α$_1$-adrenoceptor antagonists. Preferably, this invention provides a new method for inhibiting stress-activated protein kinases using compounds of Formula I:

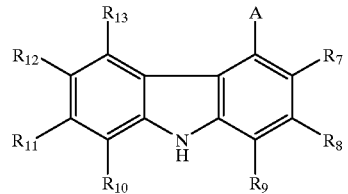

(I)

wherein:
R$_7$–R$_{13}$ are independently —H or —OH; and
A is a moiety of Formula II:

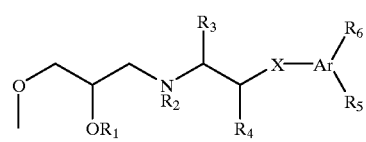

(II)

wherein:
R$_1$ is hydrogen, lower alkanoyl of up to 6 carbon atoms or aroyl selected from benzoyl and naphthoyl;
R$_2$ is hydrogen, lower alkyl of up to 6 carbon atoms or arylalkyl selected from benzyl, phenylethyl and phenylpropyl;
R$_3$ is hydrogen or lower alkyl of up to 6 carbon atoms;
R$_4$ is hydrogen or lower alkyl of up to 6 carbon atoms, or when X is oxygen, R$_4$ together with R$_5$ can represent —CH$_2$—O—;
X is a single bond, —CH$_2$, oxygen or sulfur;
Ar is selected from phenyl, naphthyl, indanyl and tetrahydronaphthyl;
R$_5$ and R$_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or
R$_5$ and R$_6$ together represent methylenedioxy; and pharmaceutically acceptable salts thereof.

More preferably, the present invention provides a new method for inhibiting stress-activated protein kinases using compounds of Formula III:

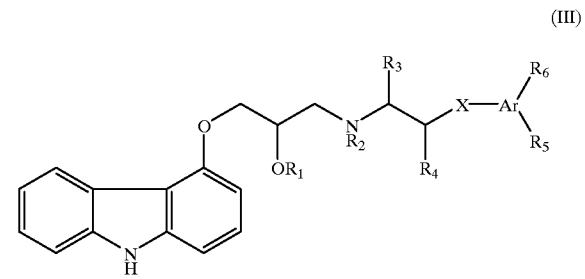

(III)

wherein:
R$_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur,

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkylsulphinyl of up to 6 carbon atoms and lower alkylsulphonyl of up to 6 carbon atoms; or $R_5$ and $R_6$ together represent methylenedioxy; and pharmaceutically acceptable salts thereof.

Most preferably, the present invention provides a new method for inhibiting stress-activated protein kinases using a compound of Formula IV, better known as carvedilol or (1-(carbazol-4-yloxy-3-[[2-(o-methoxyphenoxy)ethyl] amino]-2-propanol):

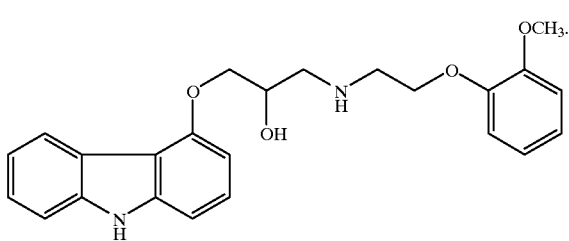

(IV)

The compounds of the present invention are novel multiple action drugs useful in the treatment of mild to moderate hypertension. Carvedilol is known to be both a competitive non-selective β-adrenoceptor antagonist and a vasodilator, and is also a calcium channel antagonist at higher concentrations. The vasodilatory actions of carvedilol result primarily from $α_1$-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug in animals, particularly in humans. See Willette, R. N., Sauermelch, C. F. & Ruffolo, R. R., Jr. (1990) Eur. J. Pharmacol., 176, 237–240; Nichols, A. J., Gellai, M. & Ruffolo, R. R., Jr. (1991) Fundam. Clin. Pharmacol., 5, 25–38; Ruffolo, R. R., Jr., Gellai, M., Hieble, J. P., Willette, R. N. & Nichols, A. J. (1990) Eur. J. Clin. PharmacoL, 38, S82-S88; Ruffolo, R. R., Jr., Boyle, D. A., Venuti, R. P. & Lukas, M. A. (1991) Drugs of Today, 27, 465–492; and Yue, T. -L., Cheng, H., Lysko, P. G., Mckenna, P. J., Feuerstein, R., Gu, J., Lysko, K. A., Davis, L. L. & Feuerstein, G. (1992) J. Pharmacol. Exp. Ther., 263, 92–98.

The antihypertensive action of carvedilol is mediated primarily by decreasing total peripheral vascular resistance without causing the concomitant reflex changes in heart rate commonly associated with other antihypertensive agents. Willette, R. N., et al. supra; Nichols, A. J., et al. supra; Ruffolo. R. R., Jr., Gellai, M., Hieble, J. P., Willette, R. N. & Nichols, A. J. (1990) Eur. J. Clin. Pharmacol., 38, S82–S88 . . . Carvedilol also markedly reduces infarct size in rat, canine and porcine models of acute myocardial infarction, Ruffolo, R. R., Jr., et al., Drugs of Today, supra, possibly as a consequence of its antioxidant action in attenuating oxygen free radical-initiated lipid peroxidation. Yue, T.-L., et al. sapra.

Recently, it has been discovered that compounds which are dual non-selective β-adrenoceptor and $α_1$-adrenoceptor antagonists, in particular the compounds of Formula I, preferably carvedilol, inhibit stress-activated protein kinases. Based on this mechanism of action, the instant compounds can be used to treat diseases wherein inhibition of stress-activated protein kinases is indicated. In particular, the compounds of the present invention, preferably carvedilol, can be used for blocking SAPK-induced apoptosis, particularly in cardiac cells or in neuronal cells. Therefore, the compounds of Formula I are useful in treating cardiovascular diseases and neurodegenerative disorders.

Some of the compounds of Formula I are known to be metabolites of carvedilol. Certain preferred compounds of the present invention, that is, the compounds of Formula I wherein A is the moiety of Formula II wherein R1 is —H, R2 is —H, R3 is —H, R4 is —H, X is O, Ar is phenyl, R5 is ortho —OH, and R6 is —H, and one of $R_7$, $R_9$, or $R_{10}$ is —OH, are metabolites of carvedilol.

Compounds of Formula I may be conveniently prepared as described in U.S. Pat. No. 4,503,067. Reference should be made to said patent for its full disclosure, the entire disclosure of which is incorporated herein by reference.

Pharmaceutical compositions of the compounds of Formula I, including carvedilol, may be administered to patients according to the present invention in any medically acceptable manner, preferably orally. For parenteral administration, the pharmaceutical composition will be in the form of a sterile injectable liquid stored in a suitable container such as an ampoule, or in the form of an aqueous or nonaqueous liquid suspension. The nature and composition of the pharmaceutical carrier, diluent or excipient will, of course, depend on the intended route of administration, for example whether by intravenous or intramuscular injection Pharmaceutical compositions of the compounds of Formula I for use according to the present invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinyl-pyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Dosing in humans for the treatment of disease according to the present invention should not exceed a dosage range of from about 3.125 to about 50 mg of the compounds of Formula I, particularly carvedilol, preferably given twice daily. As one of ordinary skill in the art will readily comprehend, the patient should be started on a low dosage regimen of the desired compound of Formula I, particularly carvedilol, and monitered for well-known symptoms of intolerance, e.g., fainting, to such compound. Once the patient is found to tolerate such compound, the patient should be brought slowly and incrementally up to the maintenance dose. The choice of initial dosage most appropriate for the particular patient is determined by the practitioner using well-known medical principles, including, but not limited to, body weight. In the event that the patient exhibits medically acceptable tolerance of the compound for two weeks, the dosage is doubled at the end of the two weeks and the patient is maintained at the new, higher dosage for two more weeks, and observed for signs of intolerance. This course is continued until the patient is brought to a maintenance dose It will be appreciated that the actual preferred dosages of the compounds being used in the compositions of this invention will vary according to the particular composition formulated, the mode of administration, the particular site of administration and the host being treated.

No unacceptable toxicological effects are expected when the compounds of Formula I, including the compound of Formula II, are used according to the present invention.

The experimentals which follow are not intended to limit the scope of this invention, but are provided to illustrate how to use the compounds of this invention. Many other embodiments will be readily apparent to those skilled in the art.

Experimental

Heart perfusion and tissue extraction

Male New Zealand white rabbits (2.5–3.1 kg) were anesthetized with sodium pentobarbital, 10 mgc/kg, and the hearts removed rapidly and placed in cold Krebs-Henseleit bicarbonate-buffered saline supplemented with 10 mM glucose and equilibrated with 95% $O_2$/5% $CO_2$. The temperature of the perfusates and the hearts was maintained at 37° C. After equilibration (20 min), the perfusion was interrupted for 30 min unless otherwise indicated by switching off the perfusion pump, and the hearts were thus rendered globally ischemic. Reperfusion was initiated by restarting the pump. Carvedilol or propranolol was infused via a syringe pump to give a final concentration of 10 $\mu$M or a concentration indicated when reperfusion was started. Control hearts were perfused for up to 50 minutes after the preequilibration without interruption to the perfusate flow. At the end of the perfusion period, hearts ventricles were "freeze-clamped" using aluminum tongs precooled in liquid $N_2$ and pulverized under liquid N.. The powders were resuspended in ice-cold lysis buffer. Extracts were incubated for 5 min at 4° C. The detergent-soluble supernatant fractions were retained, and protein content was measured.

Stress-activated protein kinase (SAPK/JNK) assay

Fusion protein, GST-c-Jun$_{(1-81)}$ was made according to the method described by Hibi et al (14). The cDNA clone with a sequence encoding human c-Jun amino acids 1–81 was provided by Human Genome Sciences (HGS) (Gaithesberg, MD) and subcloned into a pGEX 4T-3 which contains a DNA sequence encoding glutathione-S-transferase (GST). The GST-cJun expression Vector, pGEX4T-3/c-Jun, was transformed into $E.Coli$. Expression of GST-c-Jun$_{(1-81)}$ fusion protein was induced by isopropyl-β-thiogalactoside (IPTG). $E.Coli$ were lysed and centrifuged. The fusion protein, GST-c-Jun$_{(1-81)}$ was purified by glutathione-Sepharose chromatography.

SAPK/JNK assay

For analysis of protein kinases that bind c-Jun ("pull-down" assays), detergent-soluble extracts (100 $\mu$L, 0.5 mg protein) were added to 4 $\mu$ of GST-c Jun$_{1-81}$. After incubation (4° C., 1 hour), glutathione-Sepharose was added, and the incubation was continued with mixing (4° C., 1 hour). Pellets were washed in lysis buffer A containing 75 mmol/L NaCl, then in buffer A (mmol/L: HEPES 20, MgCl$_2$ 2.5, ED)TA 0.1, and β-glycerophosphate 20, pH 7.7) containing 75 mrmnol/L NaCl and 0.05% (vol/vo/) Triton X-100, and finally in buffer A alone. Phosphorylation of GST-c Jun$_{1-81}$, by JNK/SAPKs was initiated with 30 $\mu$L of kinase assay buffer (mmol/L: HEPES 20, MgCl$_2$20,β-glycerophosphate 20, DTT 2, and Na$_3$ VO$_4$ 0.1, pH 7.6) containing 20 $\mu$mol/L ATP and 1 to 2 $\mu$Ci [y-$^{32}$P] ATP (Amersham International). After 20 minutes at 30° C., the reaction was terminated by centrifugation. The pellet was washed in cold buffer A containing 75 mmolnL NaCl and 0.05% (vol/vol) Triton X-100. Phosphorylated proteins in the pellet were eluted by boilingin SDS-PAGE sample buffer and then separated by SDS-PAGE. Gels were stained with Coomassie blue to identifythe 46-kD GST-c-Jun$_{1-81}$. After autoradiography phoslorlmager was used to quantify the band intensities of c-Jun$_{1-81}$.

Results

Ischemia-reperfusion activated SAPK in a time-dependent manner and peaked at 20 min after reprefusion as shown in FIG. 1.

Figure 2:
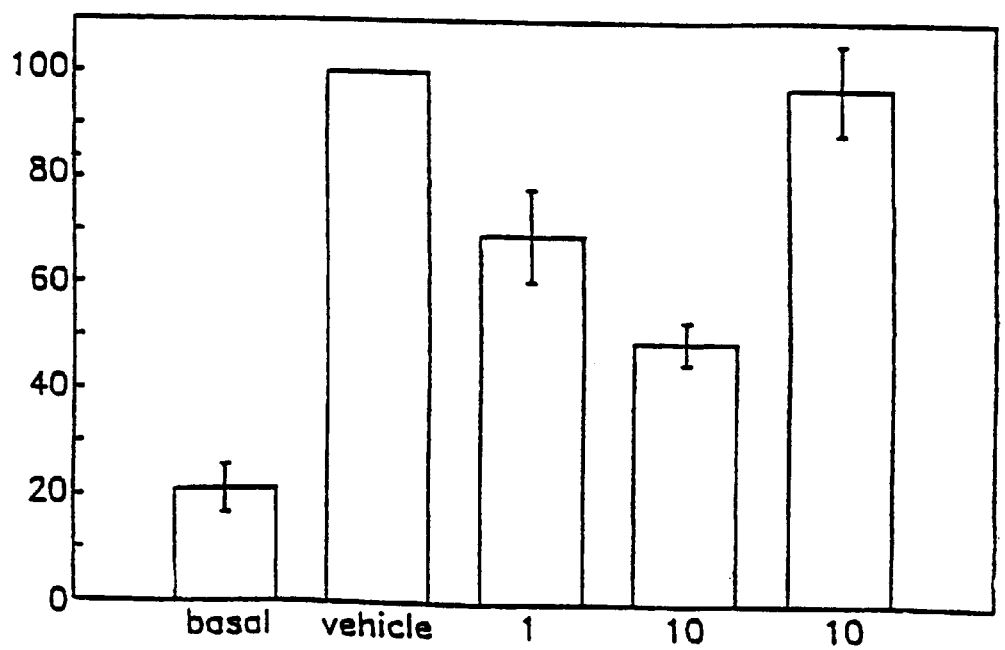

Carvedilol, administered at the beginning of reperfusion reduced the activation of SAPK by 51.2% and 30.7% at 1 and 10 $\mu$M, respectively. Under the same condition, propranolol, at 10 $\mu$M, had no effect on SAPK activation by ischemia-reperfusion as shown in FIG. 2.

The foregoing is illustrative of the use of the compounds of this invention. This invention, however, is not limited to the precise embodiment described herein, but encompasses all modifications within the scope of the claims which follow.

What is claimed is:

1. A method for inhibiting stress-activated protein kinases (SAPKs) which comprises administering to a mammal in need thereof an effective amount of a compound which is a dual non-selective β-adrenoceptor and α$_1$-adrenoceptor antagonist.

2. The method of claim 1 wherein the compound is a compound of Formula 1:

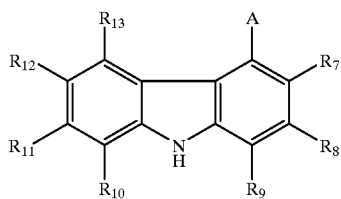
(I)

wherein:
$R_7$–$R_{13}$ are independently —H or —OH; and
A is a moiety of Formula II:

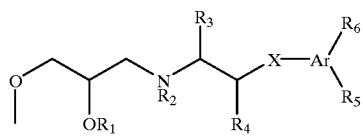
(II)

wherein:
$R_1$ is hydrogen, lower alkanoyl of up to 6 carbon atoms or aroyl selected from benzoyl and naphthoyl;
$R_2$ is hydrogen, lower alkyl of up to 6 carbon atoms or arylalkyl selected from benzyl, phenylethyl and phenylpropyl;
$R_3$ is hydrogen or lower alkyl of up to 6 carbon atoms;
$R_4$ is hydrogen or lower alkyl of up to 6 carbon atoms, or when X is oxygen, $R_4$ together with $R_5$ can represent —$CH_2$—O—;
X is a single bond, —$CH_2$, oxygen or sulfur;
Ar is selected from phenyl, naphthyl, indanyl and tetrahydronaphthyl;
$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or
$R_5$ and $R_6$ together represent methylenedioxy; or pharmaceutically acceptable salts thereof.

3. The method of claim 1 wherein the compound is a compound of Formula III:

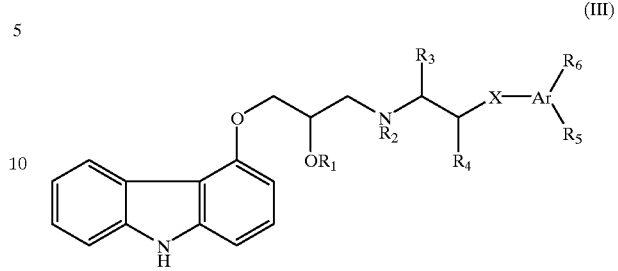
(III)

wherein:
$R_1$ is hydrogen, lower alkanoyl of up to 6 carbon atoms or aroyl selected from benzoyl and naphthoyl;
$R_2$ is hydrogen, lower alkyl of up to 6 carbon atoms or arylalkyl selected from benzyl, phenylethyl and phenylpropyl;
$R_3$ is hydrogen or lower alkyl of up to 6 carbon atoms;
$R_4$ is hydrogen or lower alkyl of up to 6 carbon atoms, or when X is oxygen, $R_4$ together with $R_5$ can represent —$CH_2$—O—;
X is a valency bond, —$CH_2$, oxygen or sulfur;
Ar is selected from phenyl, naphthyl, indanyl and tetrahydronaphthyl;
$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or or a pharmaceutically acceptable salt thereof.

4. The method according to claim 1 wherein said compound is carvedilol.

\* \* \* \* \*